(12) United States Patent
Yoneda

(10) Patent No.: US 6,595,674 B1
(45) Date of Patent: Jul. 22, 2003

(54) LIGHTING DEVICE FOR SURFACE INSPECTION

(75) Inventor: Kenji Yoneda, Kyoto (JP)

(73) Assignee: CCS Inc., Kyoto (JP)

( * ) Notice: Subject to any disclaimer, the term of this patent is extended or adjusted under 35 U.S.C. 154(b) by 0 days.

(21) Appl. No.: 09/720,649

(22) PCT Filed: Jul. 2, 1999

(86) PCT No.: PCT/JP99/03566

§ 371 (c)(1),
(2), (4) Date: Dec. 28, 2000

(87) PCT Pub. No.: WO00/01984

PCT Pub. Date: Jan. 13, 2000

(30) Foreign Application Priority Data

Jul. 2, 1998 (JP) .......................... 10-187706

(51) Int. Cl.[7] .................................. F21V 7/04
(52) U.S. Cl. .................. 362/555; 362/551; 362/554; 362/556; 362/800; 385/89; 385/115
(58) Field of Search ................. 362/555, 580, 362/551, 554, 556, 294, 373, 251, 800, 581, 572; 385/901, 88, 89, 92, 14, 115, 120

(56) References Cited

U.S. PATENT DOCUMENTS

| | | | | |
|---|---|---|---|---|
| 5,301,090 A | * | 4/1994 | Hed | 362/558 |
| 5,803,575 A | * | 9/1998 | Ansems et al. | 362/554 |
| 6,198,872 B1 | * | 3/2001 | Lipson et al. | 362/555 |

FOREIGN PATENT DOCUMENTS

| | | |
|---|---|---|
| JP | 60-49039 | 4/1985 |
| JP | 63-88808 | 6/1988 |
| JP | 2-143872 | 6/1990 |
| JP | 3-251868 | 11/1991 |
| JP | 7-272514 | 10/1995 |
| JP | 9-127424 | 5/1997 |

* cited by examiner

Primary Examiner—Sandra O'Shea
Assistant Examiner—Bertrand Zeade
(74) Attorney, Agent, or Firm—Armstrong, Westerman & Hattori, LLP (57) ABSTRACT

In a lighting device according to the present invention, light emitted from a light source (L1) is introduced to a light guide input terminal of a fiber bundle (3) in which a plurality of optical fibers (2) are bundled and is used for illumination by being emitted from a light guide output terminal (2b); the light source (L1) consists of a plurality of LEDs and the light from each LED is respectively introduced to one or more optical fibers (2).

8 Claims, 8 Drawing Sheets

LIGHTING DEVICE FOR SURFACE INSPECTION

TECHNICAL FIELD

The present invention relates to a lighting device for surface inspection used for the inspection of products etc in factories.

BACKGROUND ART

Lighting devices are employed for inspection of the external appearance and/or defects of products etc in factories. For such lighting devices, lighting devices of higher luminous intensity than that of ordinary lighting devices are often required; for these purposes, halogen lamps are often employed as the light source. Illumination of the subject of inspection is performed by directing the light emitted from a halogen lamp incorporated in the main device body of the lighting device onto one end of an optical fiber bundle comprising a plurality of optical fibers, and extracting this from the tip thereof.

However, although a halogen lamp has the advantage that high luminous intensity is obtained, the luminous intensity gradually decreases with time of use, due to evaporation etc of the filament, with the result that it becomes unusable usually after about 2000 hours. Thus, since the life of a halogen lamp is short, maintenance, involving replacement etc, must be carried out frequently and in addition, in cases where inspection with the same luminous intensity is required, since the luminous intensity gradually decreases with period of use, operation to maintain the same luminous intensity by constantly performing fine adjustment of the supplied voltage etc becomes necessary. Such maintenance or luminous intensity adjustment operations interfere with automation of the product inspection step and constitute a factor that adversely affects the inspection efficiency. Furthermore, owing to the characteristic of halogen lamps that their amount of light increases or decreases only slowly in response to turning the power source on or off, in cases where, depending on the type of inspection, it is required that the light should be turned on and off instantaneously in stroboscopic fashion, the method must be adopted of cutting off the light mechanically by means of a shutter or the like, leading to the drawback that the device becomes complicated and of large size. Also, since the halogen lamp itself is comparatively large, there is the inconvenience that making the main body of the device compact is difficult.

Although various devices have been considered in order to solve such inconveniences, it has not been possible to solve any of the above problems or solutions have been difficult to implement from the point of view of cost, so the development of a lighting device for inspection purposes that does not have these problems is desired.

DISCLOSURE OF THE INVENTION

An object of the present invention is to provide a lighting device whereby these problems are solved at a stroke and which basically adopts a construction wherein LEDs are respectively mounted at the light guide input terminals of optical fibers, and whereby an amount of light sufficient for inspection purposes can be supplied in stable fashion, and which has a long life.

In order to achieve this object, a lighting device according to the present invention for surface inspection is constituted such that light emitted from a light source is fed into the light guide input terminal of an optical fiber bundle obtained by bundling a plurality of optical fibers and is employed for illumination by being extracted from the light guide output terminal thereof, in which the light source comprises a plurality of LEDs and the light that is emitted from each of the LEDs is arranged to be respectively guided into one or more optical fibers.

By means of such a construction, since a plurality of LEDs are employed, and the light that is emitted from each of the LEDs is respectively introduced into each optical fiber (or two or more optical fibers), as a whole, luminous intensity that is fully sufficient for product inspection etc can be obtained by making the number of LEDs a large number. Furthermore, due to the characteristics of LEDs, compared with a halogen lamp, an amount of light that is much more stable can be maintained over a long period, making it possible to greatly reduce the work involved in maintenance and/or adjustment in order to maintain the luminous intensity level. Automation of the product inspection step can therefore be facilitated, and the efficiency of inspection can be raised.

Also, in order to simplify the construction and to reduce as far as possible the loss of light at the region of the junction of the optical fibers and the LEDs, it is desirable that the light guide input terminal of the optical fibers is directly bonded to the light-emitting element main bodies of the LEDs.

Also, specifically, as a preferred embodiment aimed at increasing the compactness and reducing the weight of the device, there may be mentioned a device wherein a plurality of light-emitting element main bodies that constitute the aforesaid LEDs are arranged so as to be distributed on the surface of a circuit board. The plurality of light-emitting element main bodies may be arranged distributed in matrix fashion on the surface of the printed circuit board.

When the light-emitting element main bodies are arranged distributed in this way on the printed circuit board, the amount of heat that is generated by the closely packed LEDs becomes large and tends to accumulate in the printed circuit board, so the amount of light emitted by the LEDs and their life may be reduced.

Accordingly, in order to efficiently remove this amount of heat, it is desirable to arrange a cooling device in the vicinity of said circuit board. Specifically, as such a cooling device, there may be provided a heat sink to the rear of the printed circuit board, or a Peltier element for cooling purposes may be adhered to the rear face of the circuit board. Furthermore, it is desirable to provide a heat-removing fan for introducing and circulating external atmosphere within the lighting device.

Also, in order to suppress generation of heat by the densely packed LEDs, it is desirable to provide a switch that turns on/off the supplied power of the light-emitting element main bodies. Specifically, a switch is desirable that is operated in pulse modulation mode. In this way, since the LEDs can be turned on/off in response to turning on/off of the supplied power in an extremely short time of the order of microseconds, it becomes possible to achieve a considerable reduction in the amount of heat generated by the densely packed LEDs, and, even in cases where, depending on the type of inspection, the light is required to be turned on/off instantaneously in stroboscopic fashion, this can be achieved simply by turning the power on/off, making it possible to meet such demands with an extremely simple construction.

BEST MODE FOR CARRYING OUT THE INVENTION

Figure 1:
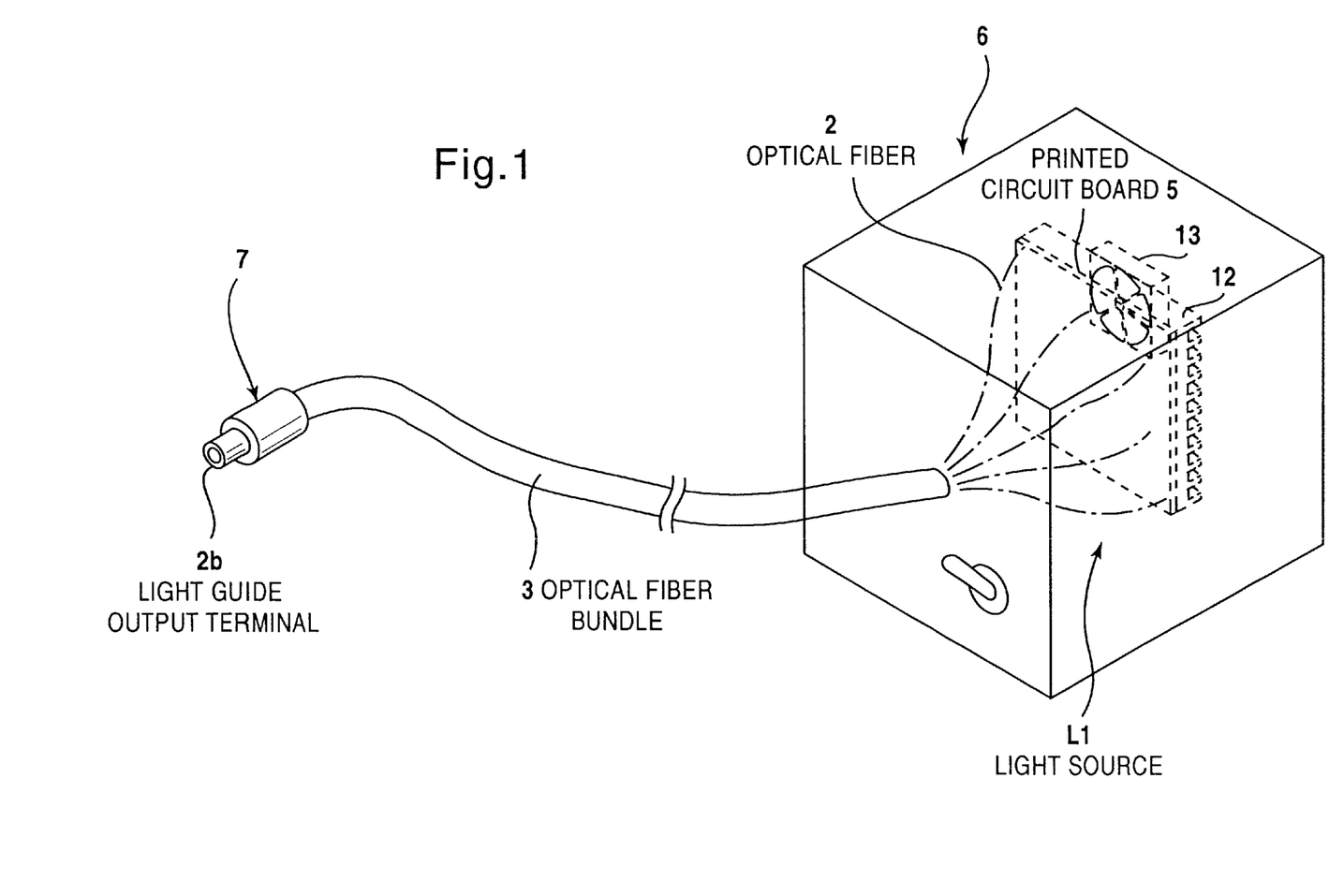
FIG. 1 is a diagrammatic overall view of a lighting device illustrating an embodiment of the present invention.

An embodiment of the present invention is described below with reference to FIG. 1 to FIG. 3.

Lighting device according to this embodiment is employed for product inspection in a factory. As shown in FIG. 1, it comprises a device main body 6 incorporating a light source L1, a lighting member 7 for illuminating the subject of inspection, and an optical fiber bundle 3 connected between the device main body 6 and lighting member 7 for directing light emitted from light source L1 onto lighting member 7.

Figure 2:
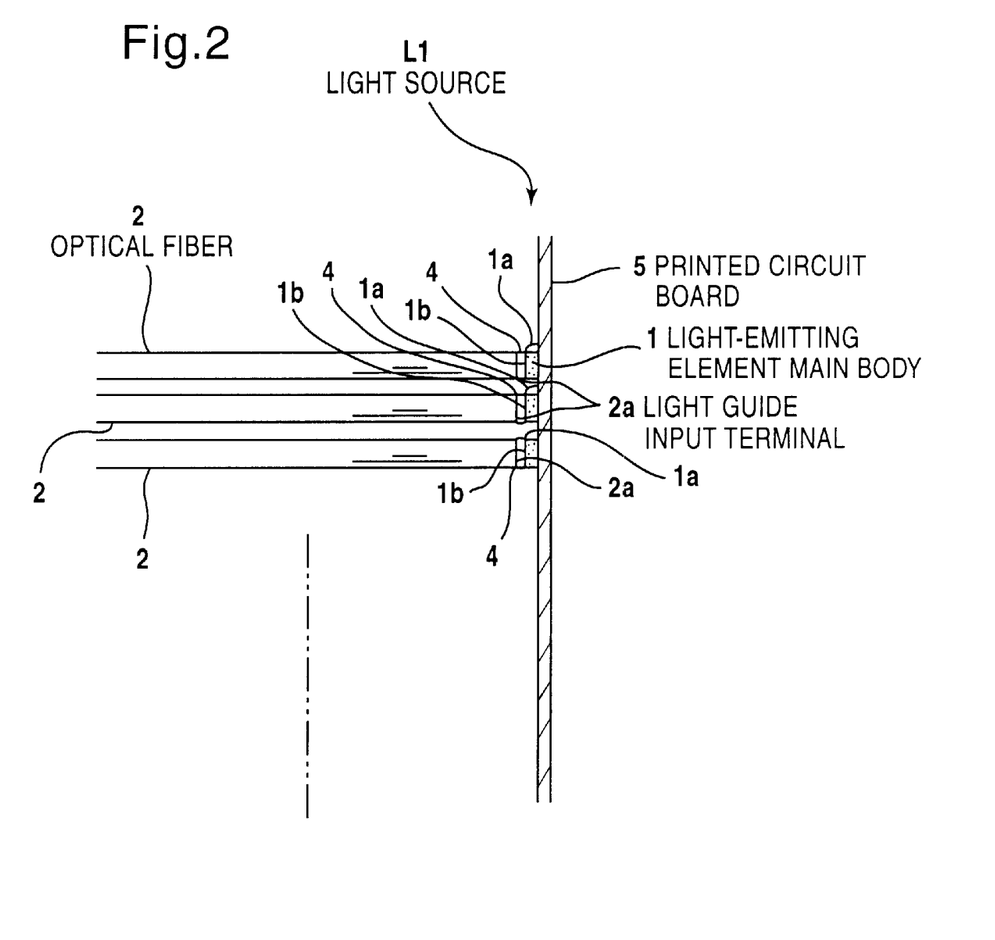
FIG. 2 is a partial cross-sectional view to a larger scale illustrating the light source part in the embodiment of FIG. 1 to a larger scale.
Figure 3:
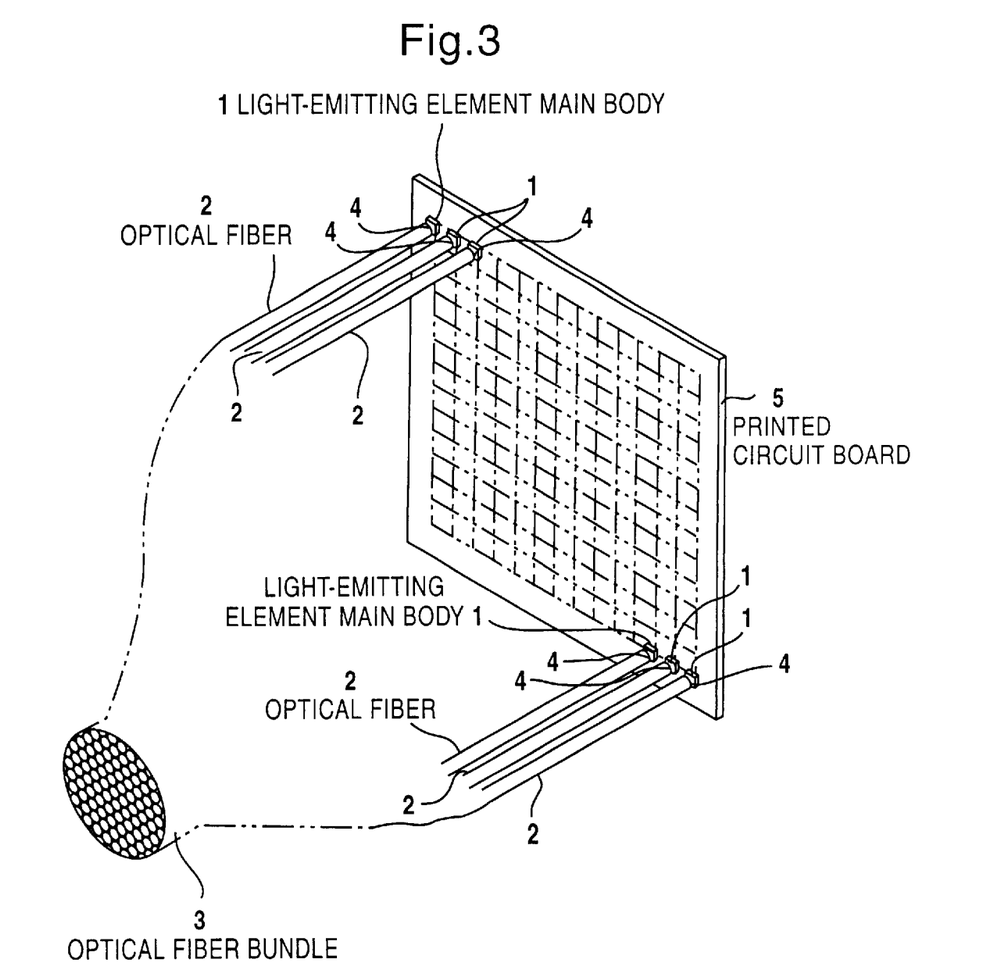
FIG. 3 is a partial perspective view illustrating the light source part in the embodiment of FIG. 1 to a larger scale.

As shown in FIG. 2 and FIG. 3, light source L1 is constituted by mounting a plurality of light-emitting element main bodies 1 constituted by LEDs in a vertical and horizontal matrix on the surface of a printed circuit board 5. Preferably light-emitting element main bodies of the surface light-emitting type are employed as light-emitting element main bodies 1; in this embodiment, those which are employed for LEDs of the so-called high luminance or ultra-high luminance type are used. The number of these is set at for example about 200, but the number will of course vary depending on the degree of luminous intensity required. Power lines, not shown, are of course provided on printed circuit board 5 for supplying power to the light-emitting element main bodies 1. The symbol 1a shown in FIG. 2 is a lead that connects the power line with the power source of each light-emitting element main body 1. At the back of the printed circuit board 5 there is stuck a heat sink 12 to remove the heat that is generated by the densely packed LEDs; a fan 13 is mounted for forcibly introducing and circulating external air in device main body 6. In addition, it is beneficial to increase the heat removal effect by sticking a Peltier element (not shown) on to the back face of printed circuit board 5.

Apart from the above, in addition, although not shown, switches etc for turning on and off the power source device and/or this power supply are incorporated within this device main body 6. Also, in this embodiment, adjustment of the amount of light of the light-emitting element main bodies 1 is performed by the so-called PWM Method (Pulse Width Modulation method), in which the power is employed in pulse form and adjustment is effected by altering the ratio of the on/off times thereof.

One optical fiber 2 is respectively connected to each of the aforesaid light-emitting element main bodies 1. Specifically, the end face 2a of optical fiber 2 i.e. its optical input terminal 2a is bonded to the light-emitting face 1b of light-emitting element main body 1 by means of light-transmitting transparent adhesive resin 4. Also, each of the optical fibers 2 that are respectively bonded to the light-emitting element main bodies 1 are formed into a bundle within device main body 6 and led out to the outside as an optical fiber bundle 3. Lighting member 7 is connected at the tip portion thereof.

Optical fiber bundle 3 is constituted by a bundle of optical fibers 2 covered with a tubular cover, the whole having flexibility and being constituted such that the lighting member 7 that is connected at the tip portion thereof can be moved into a position and attitude that can to a certain extent be freely chosen.

Figure 6:
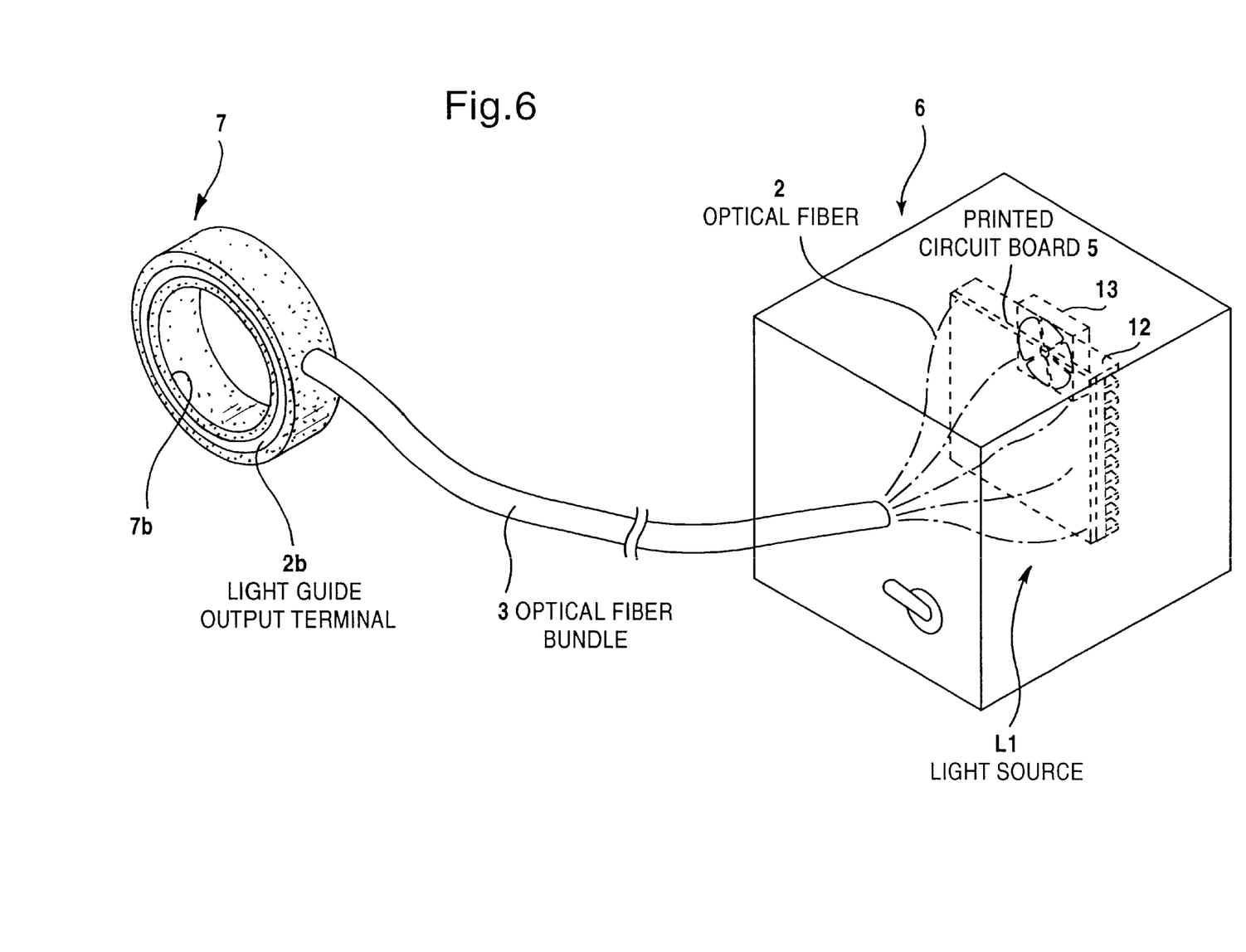
FIG. 6 is a diagrammatic overall view illustrating an example of a modification of the lighting member in a lighting device according to the present invention.

For the lighting member 7, a lighting member of well-known type is employed. In this embodiment, as shown in FIG. 1, the lighting member is of cylindrical shape, and is arranged to expose the light guide output ends 2b of a dense bundle of optical fibers 2 at its end face, so that the light that is emitted from light source L1 can perform illumination by being led out from their light guide output ends 2b through the optical fiber bundle 3. Also, as shown in FIG. 6, lighting member 7 could be of cylindrical shape, with the light guide output terminals 2b being exposed in annular fashion at its end faces. With such an arrangement, a subject of inspection can be externally viewed and inspected through the through-hole 7b of the lighting member 7, but shadows produced by illumination from the periphery of the subject of inspection can be eliminated. Lighting members fitted with a lens or lighting members of various other types may be considered as the lighting member, but, since they are well known, description of these is omitted in the present Specification.

With a lighting device according to the present embodiment constructed as above, since a large number of LED light-emitting element main bodies 1 are employed and each of the light-emitting element main bodies 1 are respectively directly connected to the optical fibers 2, as a whole, a fully sufficient luminous intensity for product inspection etc can be obtained, making it possible to reduce as far as possible loss of the amount of light in the region of the junction of the optical fibers 2 and light-emitting element main bodies 1. Furthermore, since, compared with a halogen lamp, due to the characteristics of an LED, a much more stable amount of light can be maintained over a long period, operations relating to maintenance and/or adjustment to maintain the luminous intensity can be considerably reduced. Automation of the product inspection step is therefore facilitated, making it possible to improve the efficiency of inspection. Also, since the LED light-emitting element main bodies 1 can be turned on or off in response to turning on or off of the power supply in an extremely short time of the order of microseconds, the amount of heat generated by the closely packed LEDs is greatly reduced, and even when instantaneous turning of the light on and off in stroboscopic fashion is required, depending on the type of inspection, this can be achieved simply by turning the power source on or off, making it possible to meet this requirement with an extremely straightforward construction.

In particular, in the present embodiment, since a plurality of light-emitting element main bodies 1 are arranged so as to be distributed vertically and horizontally on printed circuit board 5, compactness and weight reduction of light source L1 can be achieved.

Figure 4:
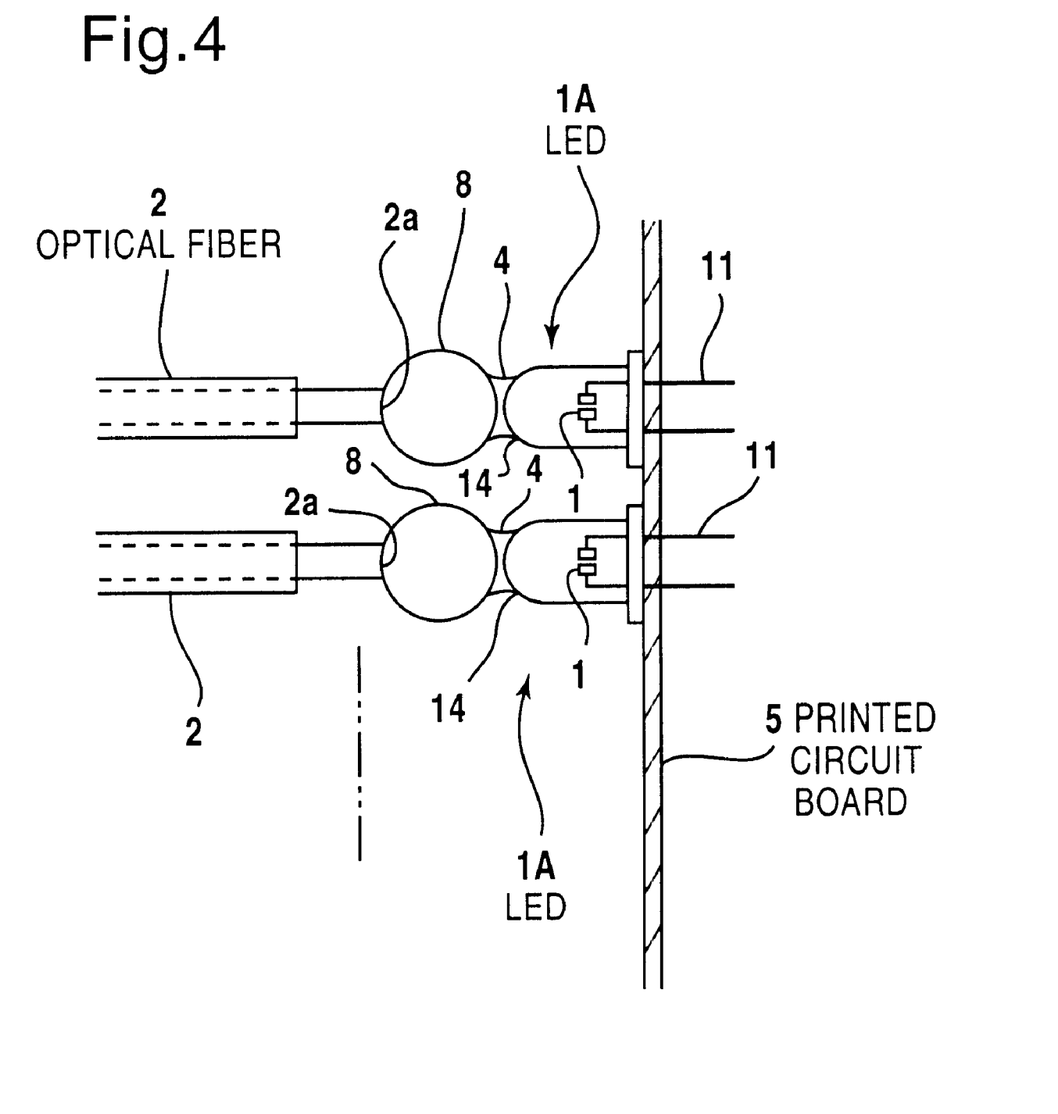
FIG. 4 is a partial perspective view illustrating the light source part in another embodiment to a larger scale.

It should be noted that the present invention is not restricted to the embodiment described above. Various modifications are indicated below, in the description of which members corresponding to those of the foregoing embodiment are given the same reference symbols. For example, as shown in FIG. 4, optical fibers 2 may be mounted on ordinary commercially available LEDs 1A wherein a power terminal 11 and transparent cover 14 etc are mounted beforehand on light-emitting element main body 1. In this case, as shown in this Figure, reduction in the amount of loss of light in this junction region is achieved by mounting LED 1A on light guide input terminal 2a of optical fiber 2 by means of a ball lens 8. Transparent adhesive resin 4 is employed to stick adjacent members together as in the embodiment described above.

Figure 5:
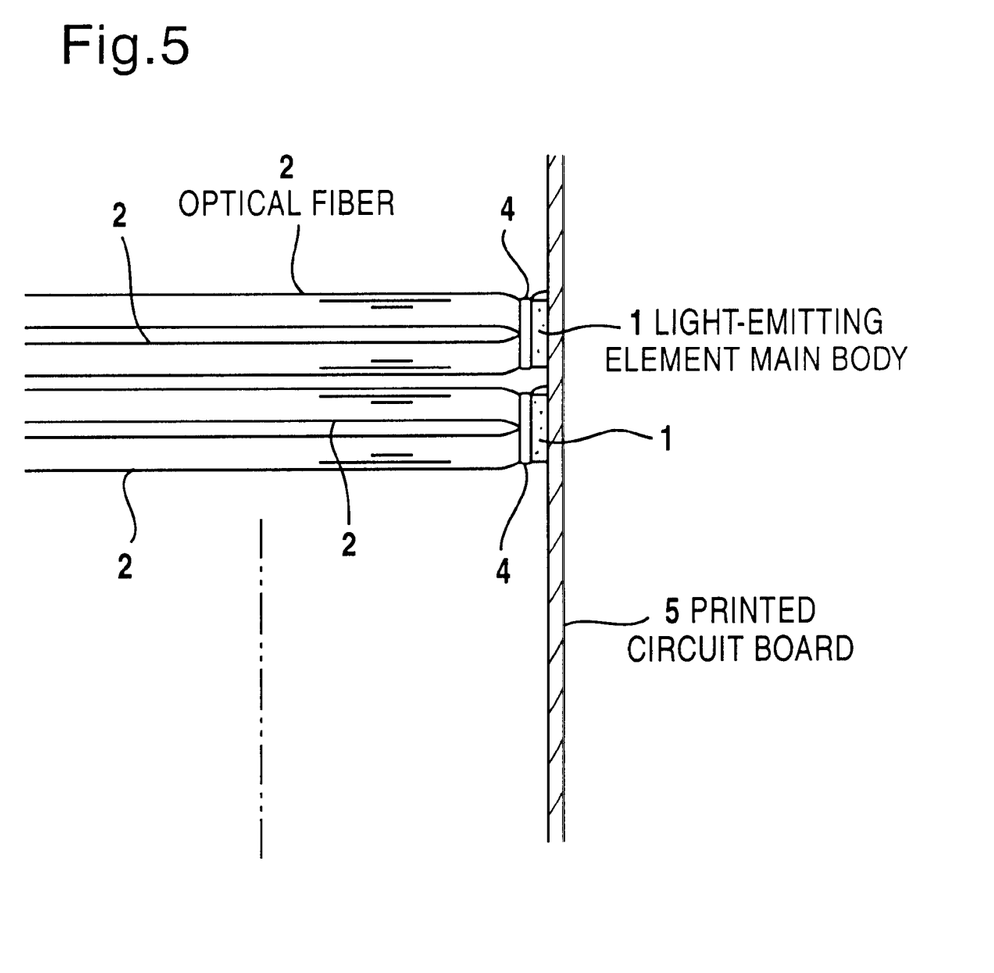
FIG. 5 is a partial cross-sectional view to a larger scale illustrating the light source part in yet a further embodiment to a larger scale.

Also, as shown in FIG. 5, two or more optical fibers 2 could be bonded to a single light-emitting element main body 1. Furthermore, various colors of the illuminating light could be set by employing in combination LEDs of different light emission color. In this way, it can be arranged to apply illumination with the optimum color for inspection, without reducing the amount of light, thereby obtaining the benefit of improving the reliability of inspection etc.

Figure 7:
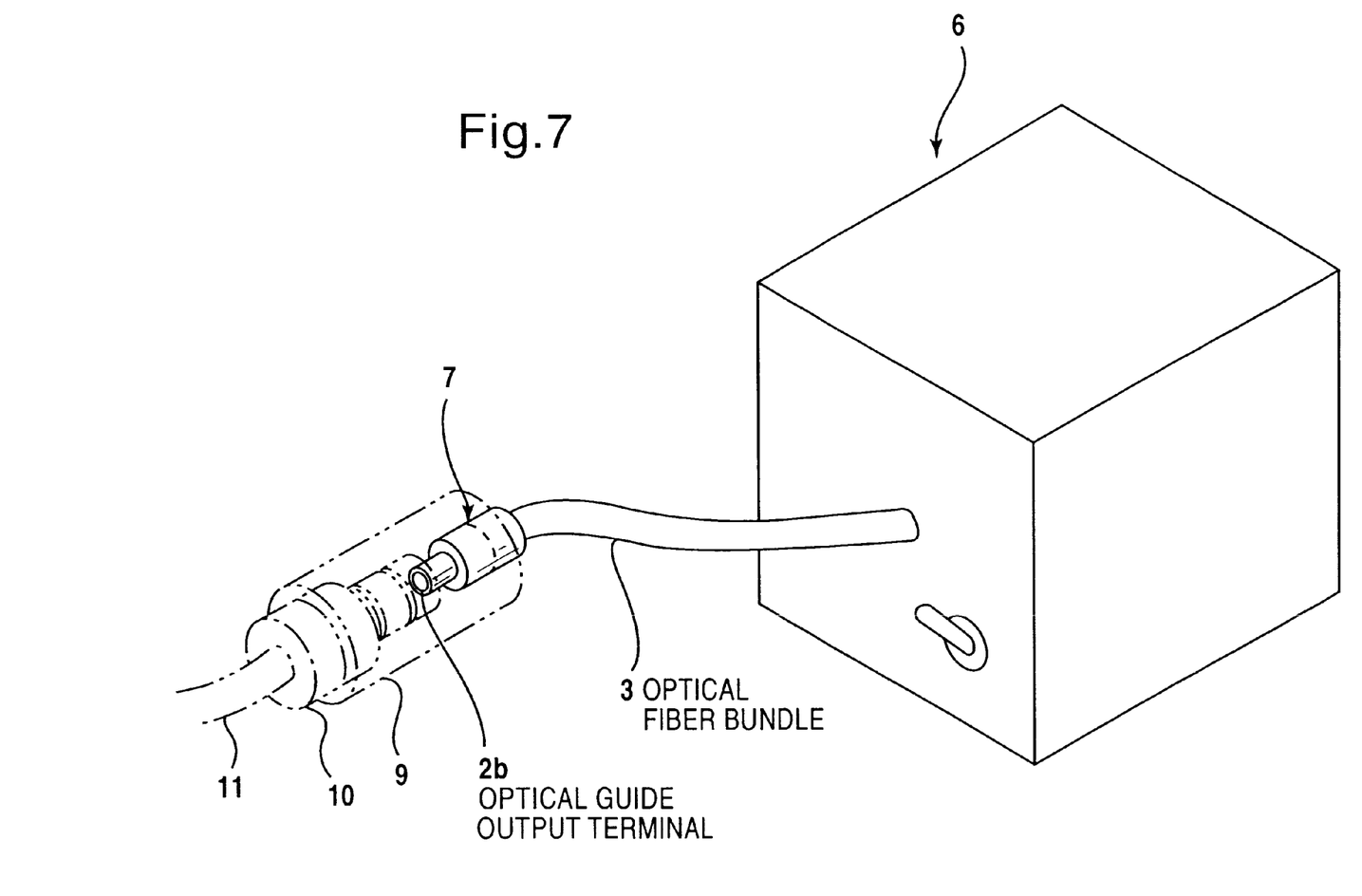
FIG. 7 is a diagrammatic overall view illustrating an example of another modification of a lighting device according to the present invention.

Also, as shown in FIG. 7, a connector 9 for connection purposes could be provided so as to enable a conventional optical fiber bundle 11 mounted on a lighting device of this kind to be used directly. If this is done, convenience in handling by the user can be improved. Reference symbol 10 is a connector for purposes of connection with the device main body mounted at the base of optical fiber bundle 11 in a prior art device. Of course, such a connector for connection purposes can be directly mounted on the outside face of this device main body 6 so as to connect the optical fiber bundle 11 employed in the conventional device. Furthermore, connection of the LEDs and optical fibers is not restricted to the methods of the above embodiments and the lighting member can be replaced by lighting members of various other types. Apart from this, the present invention is not restricted to the examples illustrated and can be modified in various ways without departing from its essence.

Figure 8A:
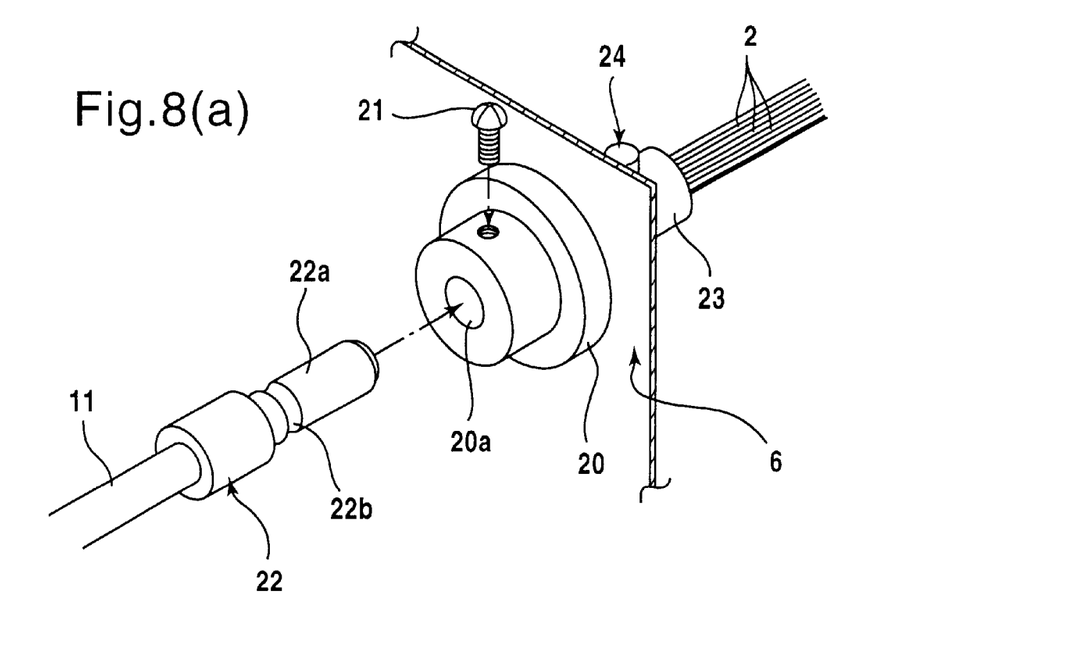
FIG. 8 is a diagram illustrating an embodiment of a connector in a lighting device according to the present invention.
Figure 8B:
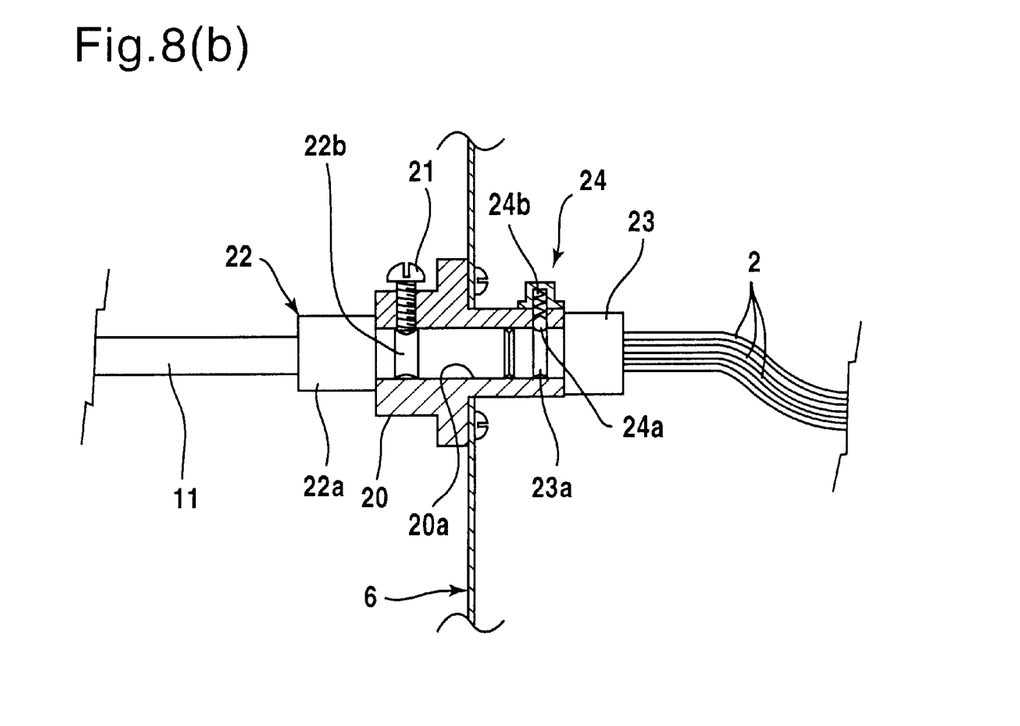

For example, there may be mentioned an arrangement wherein, as shown in FIG. 8, an existing light guide 22 and a light guide output terminal according to the present invention are connected by providing a connector 20 on device main body part 6. FIG. 8(a) is a perspective view showing the external appearance of this connector 20; FIG. 8(b) is a detail cross-sectional view showing the condition in which a light guide 22 is fixed in connector 20. The plurality of optical fibers 2 that are led out from the aforementioned LEDs are fixed in a bundle by inserting into a tip member 23, which is hollow, and the leading end face of this optical fiber bundle is polished to form a light guide output terminal. Also, this tip member 23 is fitted into a connection hole 20a of connector 20, and is fixed in position in connector 20 by means of a ball detent mechanism 24 constituted by fixing a ball 24a to the tip of spring 24b. Specifically, tip member 23 is fixed in connector 20 by engagement of ball 24a that is resiliently biased by means of spring 24b with an annular groove 23a of tip member 23. The light guide inlet terminal of a light-receiving member 22a and the light guide output terminal according to the present invention are connected by applying pressure by engagement of a screw 21 with annular groove 22b of this light-receiving member 22a with a light-receiving member 22a of light guide 22 fitted into connecting hole 20a of this connector 20. The shape of connector 20 is not restricted to that of this embodiment but could be suitably selected so as to match the shape of the light-receiving member of another existing light guide etc.

As described in detail above, the actions and benefits of the present invention are as follows.

Since a plurality of LEDs are employed and the light that is emitted from the LEDs is respectively introduced into the optical fibers (or two or more optical fibers), as a whole, a luminous intensity that is fully sufficient for inspection of products etc can be obtained by making the number of LEDs a large number. This therefore makes it possible to employ LEDs in a lighting device of this type in which conventionally a halogen lamp was employed as light source for reasons of luminous intensity. Thus, as a result, various benefits are obtained by exploiting the characteristics of LEDs. Specifically, since, compared with a halogen lamp, due to the characteristics of an LED, a much more stable amount of light can be maintained over a long period, work relating to maintenance and/or adjustment to maintain the luminous intensity can be considerably reduced. When used in product inspection, automation of this step is therefore facilitated, making it possible to improve the efficiency of inspection.

In addition, since the light source is constituted of an assembly of a plurality of LEDs, various colors of the illuminating light could be set in a simple manner by employing in combination LEDs of different light emission color, without reducing the luminous intensity as a whole. Consequently, the benefits of improving the reliability of inspection etc can be obtained by adjusting so as to provide an optimum illumination color in accordance with the subject of inspection.

Also, if the light guide input end of the optical fiber is directly bonded to the LED light-emitting element main body, simplification of the construction can be achieved and loss of light at the region of the junction of the optical fibers and LEDs can be reduced as far as possible. If in this case a plurality of light-emitting element main bodies are arranged so as to be distributed vertically and horizontally on the printed circuit board, this contributes to automating assembly and to improving the compactness of the light source.

Also, if a large number of light-emitting element main bodies are densely arranged on the circuit board so as to obtain a sufficient luminous intensity that is necessary for product inspection and for increasing the compactness of the light source etc, since the amount of heat that is generated by the closely packed LEDs is removed by arranging a cooling device in the vicinity of the aforesaid substrate, accumulation of this amount of heat on the circuit board is prevented, and so reduction in the amount of light emitted by the LEDs is prevented and the life of the LEDs can be extended.

Furthermore, thanks to the provision of a switch that turns the supplied power of the light-emitting element main bodies on/off, the LEDs react in an extremely short time, of the order of microseconds, to turning on or off of the supplied power and the amount of heat generated by the densely packed LEDs is greatly reduced, so reduction of the amount of light generated by the LEDs can be prevented and the life of the LEDs extended; also, even in cases where, depending on the type of inspection, instantaneous turning of the light on and off in stroboscopic fashion is required, this demand can be met simply by turning the power source on and off.

INDUSTRIAL APPLICABILITY

As described above, the present invention is particularly applicable in the field of lighting devices for inspection that are used to illuminate a product etc for purposes of examining the external appearance of the product etc or for finding surface defects etc.

What is claimed is:

1. A lighting device for surface inspection, comprising:

a light source including a plurality of LEDs; and an optical fiber bundle including a plurality of optical fibers, the optical fiber bundle having a light guide input terminal at one end of the bundle from which light emitted from a light source is fed, and a light guide output terminal at other end of the bundle from which light is extracted for illumination, wherein light emitted from each of the LEDs is guided into one optical fiber, and the light guide input terminal of the optical fibers is directly bonded to the LEDs, and wherein the LEDs are arranged in matrix over the surface of the board.

2. The lighting device for surface inspection according to claim 1, wherein a cooling device is provided in the vicinity of said board.

3. The lighting device for surface inspection according to claim 2, wherein, as said cooling device, a heat sink is provided in the rear of said board.

4. The lighting device for surface inspection according to claim 3, wherein a Peltier element for cooling purpose is adhered to the rear face of said board.

5. The lighting device for surface inspection according to claim 2, wherein, as said cooling device, a heat dissipating fan for introducing and circulating external air to the lighting device is provided.

6. The lighting device for surface inspection according to claim 1, comprising a switch that turns on/off supplied power of said light-emitting element main bodies.

7. The lighting device for surface inspection according to claim 6, wherein said switch is operated in pulse modulation mode.

8. A lighting device for surface inspection according to claim 1, wherein reduction in the amount of loss of light in the junction region is achieved by mounting LED on light guide input terminal of optical fiber by means of a ball lens.

* * * * *